United States Patent [19]

Morikawa et al.

[11] Patent Number: 5,426,253
[45] Date of Patent: Jun. 20, 1995

[54] PROCESS FOR PRODUCING 1,1,1,2-TETRAFLUOROETHANE

[75] Inventors: Shinsuke Morikawa, Yokohama; Shunichi Samejima, Tokyo; Masaru Yositake, Yokohama; Shin Tatematsu, Tokyo, all of Japan

[73] Assignee: Asahi Glass Company Ltd., Tokyo, Japan

[21] Appl. No.: 308,612

[22] Filed: Sep. 19, 1994

Related U.S. Application Data

[63] Continuation of Ser. No. 161,452, Dec. 6, 1993, abandoned, which is a continuation of Ser. No. 583, Jan. 4, 1993, abandoned, which is a continuation of Ser. No. 888,272, May 26, 1992, abandoned, which is a continuation of Ser. No. 369,020, Jun. 21, 1989, abandoned.

[30] Foreign Application Priority Data

Jun. 21, 1988 [JP] Japan ................. 63-151187
Jun. 21, 1988 [JP] Japan ................. 63-151188
Jun. 21, 1988 [JP] Japan ................. 63-151189
Feb. 21, 1989 [JP] Japan ................. 1-39206
Feb. 21, 1989 [JP] Japan ................. 1-39207
Feb. 21, 1989 [JP] Japan ................. 1-39208

[51] Int. Cl.$^6$ ............................................. C07C 19/08
[52] U.S. Cl. ................................................... 570/176
[58] Field of Search ...................................... 570/176

[56] References Cited

U.S. PATENT DOCUMENTS 3,439,052  4/1969  Bjornson ................. 570/176

FOREIGN PATENT DOCUMENTS 523821  4/1956  Canada .
2822471  8/1989  Germany .
1578933  11/1980  United Kingdom ......... 570/176

OTHER PUBLICATIONS

Patent Abstract of Japan vol. 13, No. 384, Nr. 1,132,537 Asahi Glass, Aug. 1989.
Patent Abstracts of Japan, vol. 13, No. 384, Nr. 1,132,638, Aug. 1989 Asahi Glass.
Patent Abstracts of Japan vol. 13, No. 379, Nr. 1,128,942, Aug. 1989 Asahi Glass.

*Primary Examiner*—Alan Siegel
*Attorney, Agent, or Firm*—Oblon, Spivak, McClelland, Maier, & Neustadt

[57] ABSTRACT

A process for producing 1,1,1,2-tetrafluoroethane, which comprises reacting 2,2-dichloro-1,1,1,2-tetrafluoroethane, 2-chloro-1,1,1,2-tetrafluoroethane or a mixture thereof with hydrogen in the presence of a hydrogenation catalyst consisting essentially of a Group VIII element as the main component and at least one element selected from the group consisting of Group IB elements, lanthanum and lanthanide elements, as an additional component.

9 Claims, No Drawings

PROCESS FOR PRODUCING 1,1,1,2-TETRAFLUOROETHANE

This application is a Continuation of application Ser. No. 08/161,452, filed on Dec. 6, 1993, which is a CON of Ser. No. 08/000,583 filed Jan. 4, 1993, which is a CON of Ser. No. 07/888,272 filed May 26, 1992 which is a CON of Ser. No. 07/369,020 filed Jun. 21, 1989 all abandoned.

The present invention relates to a process for producing R-134a (1,1,1,2-tetrafluoroethane) which is a prospective substitute for R-12 (dichlorodifluoro methane).

For the production of R-134a, a method may be mentioned wherein a haloethane starting material having four or five fluorine atoms represented by the formula $CF_2XCFYZ$ wherein X is fluorine or chlorine; provided that when X is fluorine, each of Y and Z is chlorine, fluorine or hydrogen; when one of Y and Z is fluorine, the other of Y and Z is hydrogen or chlorine; and when X is chlorine, one of Y and Z is fluorine and the other of Y and Z is chlorine or hydrogen, is reacted with hydrogen in the presence of a hydrogenation catalyst. Here, a typical haloethane starting material is 2,2-dichloro-1,1,1,2-tetrafluoroethane ($CF_3CCl_2F$). In this method, two chlorine atoms are removed from the haloethane starting material and substituted by hydrogen.

In this reaction, hydrogen chloride is produced as a by-product, as shown by the following equations, whereby the catalyst is required to have acid resistance.

$$-CF_3CCl_2F + H_2 \longrightarrow CF_3CHClF + HCl$$
$$\quad\text{(R-114a)} \quad\quad\quad\quad\quad\quad \text{(R-124)}$$

$$CF_3CHClF + H_2 \longrightarrow CF_3CH_2F + HCl$$
$$\quad\text{(R-124)} \quad\quad\quad\quad\quad\quad \text{(R-134a)}$$

As such a catalyst, it has been reported to employ palladium as a relatively inexpensive noble metal (Japanese Examined Patent Publication No. 38131/1981). However, this catalyst has drawbacks such that the durability is not necessarily adequate, and the selectivity for R-134a as the desired product is not adequate, whereby formation of R-143a ($CF_3CH_3$) as an excessively reduced product tends to be substantial.

Among platinum group elements, palladium has a relatively low melting point. Accordingly, with palladium, the temperature at which movement of atoms becomes active, is relatively low. Therefore, sintering of fine particles of palladium is considered to be one of the factors which make the useful life of the catalyst inadequate.

On the other hand, this reaction is a successive reaction as shown below and produces substantial amounts of R-124 ($CF_3CHClF$) and R-143a ($CF_3CH_3$) in addition to the desired product. Therefore, it has been desired to develop a catalyst having excellent selectivity for R-134a. It is particularly important to control the formation of R-143a which is produced by further reduction of the desired product R-134a.

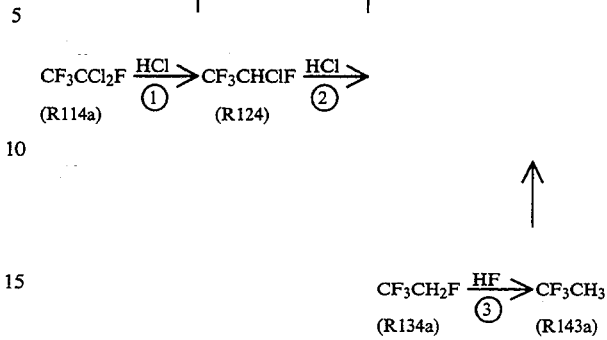

The above series of reactions are heterogeneous reactions which take place at the catalyst surface, whereby adsorption of a reactant on the catalyst surface is essential. Namely, although the micromechanism of this reaction has not yet been clearly understood, it is believed that hydrogen molecules in the gas phase are adsorbed on the catalyst surface, and the adsorbed hydrogen atoms and the haloethane are reacted at the catalyst surface, whereby the reduction reaction proceeds. Among the three reaction stages, stages ① and ② are dehydrochlorination reactions, whereas stage ③ is a dehydrofluorination reaction. The activating energy for the reaction of stage ③ is believed to be higher than stages ① and ②. Therefore, in order to control the formation of R-143a, it is believed effective to control the adsorption of R-134a on the catalyst surface and to reduce the average residence time. Adsorption of molecules on a solid surface is influenced by various factors in a complicated fashion and can not definitely be defined. However, generally speaking, the type of molecules to be adsorbed, the electron structure on the solid surface and the geometric factor, constitute important factors. The chemical adsorption energy is related to the number of d-electrons, and a transition element having a d-shell which is not filled, has a large adsorption energy. The number of d-electrons of a Group VIII element such as Pt, Pd, Ni, Rh, Co or Ru, which is excellent in the hydrogenation activity among transition elements, is within a range of from 6 to 10, and thus the d-shell is relatively highly filled. Among them, Pd and Pt tend to have particularly low adsorption energy with the number of d-electrons being 9 and 10, respectively.

Now, the geometric factor will be discussed. The above-mentioned series of molecules have very stable $CF_3$ groups. When the reaction takes place at the catalyst surface, the interaction between the CXYZ group (wherein each of X, Y and Z is hydrogen, chlorine or fluorine) located at the opposite side to the $CF_3$ group and the catalyst surface, is believed to be important. In the above reaction scheme, R-114a and R-124 have large molecular sizes, since they have two large chlorine atoms and one large chlorine atom, respectively. Whereas R-134a and R-143a have no chlorine atoms and thus smaller sizes than the above haloethanes. In order to facilitate the reactions of stages ① and ② and to suppress the reaction of stage ③, it is believed effective that the lattice constant of the catalyst metal is enlarged to suppress the adsorption of R-134a molecules containing no chlorine atoms and thus having a small size. The enlargement of the lattice constant can be attained by adding and inserting an element having low adsorption energy and thus having low catalytic activities among the catalyst atoms, or by adding and alloying a metal atom having a large lattice constant. As the additional element, at least one element selected from the group consisting of Group IB elements, lanthanum and lanthanide elements, is selected as an element which is corrosion resistant during the above reaction and which does not constitute a catalyst poison, among typical elements having their d-electron shells fully filled.

On the basis of these fundamental principles, optimization of the combination of alloy elements, their proportions and the condition for the preparation of the catalyst, has been studied. As a result, the present invention has been accomplished with a catalyst having excellent durability and selectivity.

The present invention provides a process for producing 1,1,1,2-tetrafluoroethane, which comprises reacting 2,2-dichloro-1,1,1,2-tetrafluoroethane, 2-chloro-1,1,1,2-tetrafluoroethane or a mixture thereof with hydrogen in the presence of a hydrogenation catalyst consisting essentially of a Group VIII element as the main component and at least one element selected from the group consisting of Group IB elements, lanthanum and lanthanide elements, as an additional component.

Now, the present invention will be described in detail with reference to the preferred embodiments.

When a catalyst is alloyed, it is usual in many cases that characteristics of the constituting elements appear depending upon the composition. However, when a Group IB element, lanthanum or a lanthanide element is added to a Group VIII element, no substantial reduction in the reducing activities appears, although the reason has not yet been clearly understood.

The element selected from the group consisting of Group IB elements, lanthanum and lanthanide elements, is incorporated in the catalyst usually in an amount of from 0.01 to 90% by weight, preferably from 0.1 to 30% by weight, to effectively induce hydrogenation and reducing activities of the Group VIII element.

However, the Group IB element has a relatively low melting point and is not necessarily suitable for the purpose of suppressing sintering. For this purpose, an additional component is preferably a metal having a high melting point and acid resistance. Namely, for this purpose, it is preferred to employ at least one high melting point metal element selected from the group consisting of Group VIII elements other than the element used as the main component, nickel, cobalt, rhenium, tungsten, tantalum, niobium, titanium, zirconium and molybdenum, as a second additional component. Such a second additional component is incorporated usually in an amount of from 0.01 to 20% by weight, preferably from 0.1 to 10% by weight.

In the present invention, the hydrogenation catalyst may be supported on a carrier such as active carbon, alumina or zirconia. A conventional method for the preparation of a noble metal catalyst may be used as the method for supporting the catalyst on the carrier. In use, at least a part of such a metal compound is reduced.

A platinum group catalyst is usually prepared by a method wherein ions containing the catalyst component are adsorbed on a carrier by a dipping method, followed by reduction. The properties of the catalyst substantially vary depending upon the reducing method. Reducing methods may generally be classified into a so-called wet reduction method wherein a catalyst component is adsorbed on a carrier at a temperature of around room temperature, followed by reduction in a solution, and a gas phase reduction method wherein the adsorbed carrier is dried and then reduced in a hydrogen stream. In the gas phase reduction method, it is usual that a catalyst component is supported on a carrier, followed by washing with water to remove a free ion component, then the catalyst is dried, and hydrogenation reduction is conducted at a relatively high temperature. Therefore, the method has a drawback that even when the catalyst component is adsorbed in a highly dispersed state, recoagulation of the catalyst component is likely to take place during the washing with water, drying or reduction. Further, the density of the catalyst component adsorbed on the carrier surface is substantially low as compared with the wet reduction method, and during the reduction, the proportion of the crystal grain growth tends to be higher than the formation of nuclei, whereby it is difficult to form numerous fine crystal grains. The gas phase hydrogenation reduction is not necessarily advantageous also from the viewpoint of mass production as a process for producing a catalyst.

Accordingly, the wet reduction method is preferred. To have the catalyst supported on a carrier, the carrier is immersed in a solution prepared by dissolving salts of the above-mentioned various elements in water or in an organic solvent for impregnation, and then a suitable reducing agent is added thereto to conduct reduction. As such a reducing agent, formalin, hydrazine, formic acid, sodium borohydride or hydrogen may be employed. Various ion species or molecules are densely adsorbed on the surface of the carrier dipped in the solution, whereby the crystal growth during the reduction is suppressed, and formation of nuclei will be predominant, and a catalyst having a fine particle size can readily be obtained, coupled with an advantage that the reducing temperature is low.

It is also effective to add a suitable dispersing agent. After completion of the reduction, washing and drying are conducted to obtain a catalyst. The proportions of hydrogen and the starting material may be varied within wide ranges. However, it is usual to employ a stoichiometric amount of hydrogen to substitute the halogen atoms. A substantially larger amount than the stoichiometric amount, e.g. 4 mols or higher of hydrogen, may be employed relative to the total molar amount of the starting material. With respect to the pressure for the reaction, atmospheric pressure or an elevated pressure may be employed.

The reaction temperature is preferably at least 120° C. The reaction is preferably conducted in a gas phase at a temperature of not higher than 450° C., in view of the selectivity in the reaction and the useful life of the catalyst.

The contact time is usually from 0.1 to 300 seconds, particularly from 2 to 120 seconds, when the reaction is conducted in a gas phase.

The present invention provides a process which has an advantage such that production of by-product R-143a ($CF_3CH_3$) is small, and thus R-134a ($CF_3CH_2F$) can be produced highly selectively.

Now, the present invention will be described in detail with reference to Examples. However, it should be understood that the present invention is by no means restricted to such specific Examples.

PREPARATION EXAMPLE 1-1

Active carbon made of coconut shell was immersed in pure water to impregnate water into pores thereof. An aqueous solution having palladium chloride and copper sulfate dissolved in a weight ratio of the respective metal components of 90:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 250° C. for 5 hours.

PREPARATION EXAMPLE 1-2

Active carbon made of coconut shell was immersed in pure water to impregnate water into pores thereof. An aqueous solution having palladium sulfate and silver nitrate dissolved in a weight ratio of the respective metal components of 90:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 250° C. for 5 hours.

PREPARATION EXAMPLE 1-3

Active carbon made of coconut shell was immersed in pure water to impregnate water into pores thereof. An aqueous solution having palladium chloride and chloroauric acid dissolved in a weight ratio of the respective metal components of 90:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 500° C. for 4 hours and the reduced by introducing hydrogen and maintaining it at 250° C. for 5 hours.

PREPARATION EXAMPLE 1-4

Active carbon made of coconut shell was immersed in pure water to impregnate water into pores thereof. An aqueous solution having palladium chloride, chloroplatinic acid and chloroauric acid dissolved in a weight ratio of the respective metal components of 90:2:8 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 250° C. for 5 hours.

PREPARATION EXAMPLE 1-5

Active carbon made of coconut shell was immersed in pure water to impregnate water into pores thereof. An aqueous solution having palladium chloride, rhodium chloride and chloroauric acid dissolved in a weight ratio of the respective metal components of 90:1:9 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 250° C. for 5 hours.

PREPARATION EXAMPLE 1-6

Active carbon made of coconut shell was immersed in pure water to impregnate water into pores thereof. An aqueous solution having palladium chloride, iridium chloride and chloroauric acid dissolved in a weight ratio of the respective metal components of 90:1:9 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 250° C. for 5 hours.

PREPARATION EXAMPLE 1-7

Active carbon made of coconut shell was immersed in pure water to impregnate water into pores thereof. An aqueous solution having rhodium sulfate and silver nitride dissolved in a weight ratio of the respective metal components of 90:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 1-8

Active carbon made of coconut shell was immersed in pure water to impregnate water into pores thereof. An aqueous solution having rhodium chloride and chloroauric acid dissolved in a weight ratio of the respective metal components of 90:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 1-9

Active carbon made of coconut shell was immersed in pure water to impregnate water into pores thereof. An aqueous solution having rhodium chloride, cobalt chloride and copper sulfate dissolved in a weight ratio of the respective metal components of 45:45:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 1-10

Active carbon made of coconut shell was immersed in pure water to impregnate water into pores thereof. An aqueous solution having rhodium sulfate, cobalt sulfate and silver nitrate dissolved in a weight ratio of the respective metal components of 50:40:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 1-11

Active carbon made of coconut shell was immersed in pure water to impregnate water into pores thereof. An aqueous solution having rhodium chloride, cobalt chloride and chloroauric acid dissolved in a weight ratio of the respective metal components of 50:40:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 1-12

Active carbon made of coconut shell was immersed in pure water to impregnate water into pores thereof. An aqueous solution having chloroplatinic acid and chloroauric acid dissolved in a weight ratio of the respective metal components of 90:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 1-13

Active carbon made of coconut shell was immersed in pure water to impregnate water into pores thereof. An aqueous solution having palladium chloride nickel chloride and copper sulfate dissolved in a weight ratio of the respective metal components of 45:45:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 1-14

Active carbon made of coconut shell was immersed in pure water to impregnate water into pores thereof. An aqueous solution having palladium sulfate, nickel sulfate and silver nitrate dissolved in a weight ratio of the respective metal components of 45:45:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 1-15

Active carbon made of coconut shell was immersed in pure water to impregnate water into pores thereof. An aqueous solution having palladium chloride, nickel chloride and chloroauric acid dissolved in a weight ratio of the respective metal components of 45:45:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 1-16

Active carbon made of coconut shell was immersed in pure water to impregnate water into pores thereof. An aqueous solution having ruthenium chloride and chloroauric acid dissolved in a weight ratio of the respective metal components of 90:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

COMPARATIVE PREPARATION EXAMPLE 1-1

Active carbon made of coconut shell was immersed in pure water to impregnate water into pores thereof. An aqueous solution having palladium chloride in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

COMPARATIVE PREPARATION EXAMPLE 1-2

Active carbon made of coconut shell was immersed in pure water to impregnate water into pores thereof. An aqueous solution having palladium chloride and nickel chloride (molar ratio: 1:1) dissolved in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

COMPARATIVE PREPARATION EXAMPLE 1-3

Active carbon made of coconut shell was immersed in pure water to impregnate water into pores thereof.

An aqueous solution having ruthenium chloride dissolved in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

EXAMPLES 1-1 TO 1-16

300 cc of the catalyst prepared in each Preparation Example was packed into a reaction tube made of Inconel 600 having an internal diameter of 2.54 cm and a length of 100 cm, and the reaction tube was immersed in a salt bath furnace.

Hydrogen and dichlorotetrafluoroethane (R-114a, purity: 95 mol %, the rest being its isomer R-114) were introduced into the reaction tube in a molar ratio of 2:1. The flow rates of hydrogen and the starting material were 100 cc/min and 50 cc/min, respectively. The reaction temperature was 200° C., and the contact time was 6.7 seconds. The composition of the gas at the outlet of the reaction tube was analyzed by gas chromatography. As a result, it was confirmed that the main reaction products were R-124, R-134a and R-143a. The selectivity for R-143a among them is shown in Table 1-1.

COMPARATIVE EXAMPLES 1-1 TO 1-3

By using the catalyst prepared in each Comparative Preparation Example, the reaction was conducted and the composition of the gas at the outlet of the reaction tube was analyzed in the same manner as in the preceding Examples. As a result, it was confirmed that the main reaction products were R-124, R-134a and R-143a. The selectivity for R-143a among them is shown in Table 1-2.

TABLE 1-1

| | Selectivity for R-143a | |
| --- | --- | --- |
| | Catalyst composition | Selectivity for R-143a (%) |
| Example 1-1 | Pd—Cu | 6 |
| Example 1-2 | Pd—Ag | 8 |
| Example 1-3 | Pd—Au | 5 |
| Example 1-4 | Pd—Pt—Au | 6 |
| Example 1-5 | Pd—Rh—Au | 8 |
| Example 1-6 | Pd—Ir—Au | 7 |
| Example 1-7 | Rh—Ag | 8 |
| Example 1-8 | Rh—Au | 9 |
| Example 1-9 | Rh—Co—Cu | 11 |
| Example 1-10 | Rh—Co—Ag | 8 |
| Example 1-11 | Rh—Co—Au | 9 |
| Example 1-12 | Pt—Au | 7 |
| Example 1-13 | Pd—Ni—Cu | 17 |
| Example 1-14 | Pd—Ni—Ag | 15 |
| Example 1-15 | Pd—Ni—Au | 16 |
| Example 1-16 | Ru—Au | 19 |

The catalysts used in the Examples showed no substantial change in their properties even upon expiration of 500 hours from the initiation of the reaction.

TABLE 1-2

| | Selectivity for R-143a | |
| --- | --- | --- |
| | Catalyst composition | Selectivity for R-143a (%) |
| COMPARATIVE EXAMPLE 1-1 | Pd | 29 |
| COMPARATIVE EXAMPLE 1-2 | Pd—Ni | 42 |
| COMPARATIVE EXAMPLE 1-3 | Ru | 83 |

PREPARATION EXAMPLE 2-1

Active carbon made of coconut shell was immersed in pure water to impregnate water into pores thereof. An aqueous solution having palladium chloride and copper sulfate dissolved in a weight ratio of the respective metal components of 95:5 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 250° C. for 5 hours.

PREPARATION EXAMPLE 2-2

Active carbon made of coconut shell was immersed in pure water to impregnate water into pores thereof. An aqueous solution having palladium chloride and copper sulfate dissolved in a weight ratio of the respective metal components of 92:8 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced at room temperature by means of hydrazine.

PREPARATION EXAMPLE 2-3

Active carbon made of coconut shell was immersed in pure water to impregnate water into pores thereof. An aqueous solution having palladium chloride and chloroauric acid dissolved in a weight ratio of the respective metal components of 90:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 500° C. for 4 hours and then reduced by introducing hydrogen and maintaining it at 250° C. for 5 hours.

PREPARATION EXAMPLE 2-4

Active carbon made of coconut shell was immersed in pure water to impregnate water into pores thereof. An aqueous solution having rhodium chloride and copper sulfate dissolved in a weight ratio of the respective metal components of 96:4 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 2-5

Active carbon made of coconut shell was immersed in pure water to impregnate water into pores thereof. An aqueous solution having rhodium sulfate and silver nitrate dissolved in a weight ratio of the respective metal components of 93:7 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 2-6

Active carbon made of coconut shell was immersed in pure water to impregnate water into pores thereof. An aqueous solution having rhodium chloride and chloroauric acid dissolved in a weight ratio of the respective metal components of 80:20 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 2-7

Active carbon made of coconut shell was immersed in pure water to impregnate water into pores thereof. An aqueous solution having chloroplatinic acid and copper sulfate dissolved in a weight ratio of the respective metal components of 96:4 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 2-8

Active carbon made of coconut shell was immersed in pure water to impregnate water into pores thereof. An aqueous solution having chloroplatinic acid and diamine silver sulfate dissolved in a weight ratio of the respective metal components of 91:9 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 2-9

Active carbon made of coconut shell was immersed in pure water to impregnate water into pores thereof. An aqueous solution having chloroplatinic acid and chloroauric acid dissolved in a weight ratio of the respective metal components of 85:15 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 2-10

Active carbon made of coconut shell was immersed in pure water to impregnate water into pores thereof. An aqueous solution having ruthenium chloride and copper sulfate dissolved in a weight ratio of the respective metal components of 99:1 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 2-11

Active carbon made of coconut shell was immersed in pure water to impregnate water into pores thereof. An aqueous solution having ruthenium chloride and copper sulfate dissolved in a weight ratio of the respective metal components of 95:5 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 2-12

Active carbon made of coconut shell was immersed in pure water to impregnate water into pores thereof. An aqueous solution having ruthenium chloride and chloroauric acid dissolved in a weight ratio of the respective metal components of 90:10 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

COMPARATIVE PREPARATION EXAMPLE 2-1

Active carbon made of coconut shell was immersed in pure water to impregnate water into pores thereof. An aqueous solution having palladium chloride in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

EXAMPLE 2-1 TO 2-3

300 cc of the catalyst prepared in each of Preparation Examples 2-1 to 2-3 was packed into a reaction tube made of Inconel 600 having an internal diameter of 2.54 cm and a length of 100 cm, and the reaction tube was immersed in a salt bath furnace.

Hydrogen and 2-chloro-1,1,1,2-tetrafluoroethane ($CF_3CHClF$) were introduced into the reaction tube in a molar ratio of 1:1. The flow rates of the hydrogen and the starting material were 200 cc/min and 200 cc/min, respectively. The reaction temperature was 250° C., and the contact time was 25 seconds. The reaction product was collected in a trap cooled to −78° C. An acid content was removed from the collected product, and the composition was analyzed by gas chromatography and $^{19}F$-NMR. As a result, it was confirmed that the main reaction products were 1,1,1,2-tetrafluoroethane ($CF_3CH_2F$) and 1,1,1-trifluoroethane ($CF_3CH_3$). The reaction rate upon expiration of 500 hours from the initiation of the reaction is shown in Table 2-1.

EXAMPLES 2-4 TO 2-6

By using the catalyst prepared in each of Preparation Examples 2-4 to 2-6, the reaction was conducted in the same manner as in Examples 2-1 to 2-3 except that the molar ratio of hydrogen to the starting material was changed to 2:1, and the contact time was changed to 20 seconds, and the reaction product was analyzed. The reaction rate upon expiration of 500 hours from the initiation of the reaction is shown in Table 2-1.

EXAMPLES 2-7 TO 2-9

By using the catalyst prepared in each of Preparation Examples 2-7 to 2-9, the reaction was conducted in the same manner as in Examples 2-1 to 2-3 except that the molar ratio of hydrogen to the starting material was changed to 1.5:1, and the contact time was 25 seconds, and the reaction product was analyzed. The reaction rate upon expiration of 500 hours from the initiation of the reaction is shown in Table 2-1.

EXAMPLES 2-10 TO 2-12

By using the catalyst prepared in each of Preparation Examples 2-10 to 2-12, the reaction was conducted in the same manner as in Examples 2-1 to 2-3 except that the reaction temperature was changed to 260° C., and the contact time was changed to 20 seconds, and the reaction product was analyzed. The reaction rate upon expiration of 500 hours from the initiation of the reaction is shown in Table 2-1.

COMPARATIVE EXAMPLE 2-1

By using the catalyst prepared in Comparative Preparation Example 2-1, the reaction was conducted in the same manner as in Example 2-1, and the composition of the gas at the outlet of the reaction tube was analyzed. As a result, it was confirmed that the main reaction products were 1,1,1,2-tetrafluoroethane ($CF_3CH_2F$) and 1,1,1-trifluoroethane ($CF_3CH_3$). The reaction rate upon expiration of 500 hours from the initiation of the reaction is shown in Table 2-1.

TABLE 2-1

| | Catalyst composition | Reaction rate (%) | Selectivity for R-134a (%) |
|---|---|---|---|
| Example 2-1 | Pd—Cu | 89 | 97 |
| Example 2-2 | Pd—Ag | 90 | 97 |
| Example 2-3 | Pd—Au | 90 | 97 |
| Example 2-4 | Rh—Cu | 90 | 96 |
| Example 2-5 | Rh—Ag | 90 | 96 |
| Example 2-6 | Rh—Au | 89 | 96 |
| Example 2-7 | Pt—Cu | 85 | 97 |
| Example 2-8 | Pt—Ag | 87 | 96 |
| Example 2-9 | Pt—Au | 86 | 97 |
| Example 2-10 | Ru—Cu | 76 | 94 |
| Example 2-11 | Ru—Ag | 74 | 95 |
| Example 2-12 | Ru—Au | 75 | 95 |
| Comparative Example 2-1 | Pd | 25 | 87 |

PREPARATION EXAMPLE 3-1

Active carbon made of coconut shell was immersed in pure water to impregnate water into pores thereof. An aqueous solution having palladium chloride, copper sulfate and potassium tungstate dissolved in a weight ratio of the respective metal components of 90:9:1 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 250° C. for 5 hours.

PREPARATION EXAMPLE 3-2

Active carbon made of coconut shell was immersed in pure water to impregnate water into pores thereof. An aqueous solution having palladium chloride, silver nitrate and potassium tungstate dissolved in a weight ratio of the respective metal components of 90:9:1 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 250° C. for 5 hours.

PREPARATION EXAMPLE 3-3

Active carbon made of coconut shell was immersed in pure water to impregnate water into pores thereof. An aqueous solution having palladium chloride, chloroauric acid and nickel chloride dissolved in a weight ratio of the respective metal components of 90:9:1 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 500° C. for 4 hours and then reduced by introducing hydrogen and maintaining it at 250° C. for 5 hours.

PREPARATION EXAMPLE 3-4

Active carbon made of coconut shell was immersed in pure water to impregnate water into pores thereof. An aqueous solution having rhodium sulfate, silver nitrate and potassium perrhenate dissolved in a weight ratio of the respective metal components of 90:9:1 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 3-5

Active carbon made of coconut shell was immersed in pure water to impregnate water into pores thereof. An aqueous solution having rhodium chloride, chloroauric acid and potassium tungstate dissolved in a weight ratio of the respective metal components of 90:8:2 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 3-6

Active carbon made of coconut shell has immersed in pure water to impregnate water into pores thereof. An aqueous solution having chloroplatinic acid, chloroauric acid and potassium perrhenate dissolved in a weight ratio of the respective metal components of 90:8:2 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 3-7

Active carbon made of coconut shell was immersed in pure water to impregnate water into pores thereof. An aqueous solution having ruthenium sulfate, silver sulfate and potassium tungstate dissolved in a weight ratio of the respective metal components of 90:9:1 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 3-8

Active carbon made of coconut shell was immersed in pure water to impregnate water into pores thereof. An aqueous solution having ruthenium chloride, chloroauric acid and ammonium molybdenate dissolved in a weight ratio of the respective metal components of 90:9:1 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

COMPARATIVE PREPARATION EXAMPLE 3-1

Active carbon made of coconut shell was immersed in pure water to impregnate water into pores thereof. An aqueous solution having palladium chloride, copper sulfate and potassium tungstate dissolved in a weight ratio of the respective metal components of 90:9:1 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

EXAMPLES 3-1 TO 3-8

300 cc of the catalyst prepared in each Preparation Example was packed into a reaction tube made of Inconel 600 having an internal diameter of 2.54 cm and a length of 100 cm, and the reaction tube was immersed in a salt bath furnace.

Hydrogen and a starting material (comprising 2,2-dichloro-1,1,1,2-tetrafluoroethane and 1,2-dichloro-1,1,2,2-tetrafluoroethane in a molar ratio of 95:5) were introduced into the reaction tube in a molar ratio of 2:1. The flow rates of hydrogen and the starting material were 100 cc/min and 50 cc/min, respectively. The reaction temperature was 200° C. and the contact time was 20 seconds. As a result, it was confirmed that the main reaction products were R-124, R-134a and R-143a. The selectivity for R-143a among them is shown in Table 3-1.

COMPARATIVE EXAMPLE 3-1

By using the catalyst prepared in Comparative Preparation Example 3-1, the reaction was conducted in the same manner as in Examples, and the composition of the gas at the outlet of the reaction tube was analyzed. As a result, it was confirmed that the main reaction products were R-124, R-134a and R-143a. The selectivity for R-143a among them is shown in Table 3-1.

TABLE 3-1

| | Selectivity for R-143a | |
|---|---|---|
| | Catalyst composition | Selectivity for R-143a (%) |
| Example 3-1 | Pd—Cu—W | 6 |
| Example 3-2 | Pd—Ag—W | 5 |
| Example 3-3 | Pd—Au—Ni | 5 |
| Example 3-4 | Rh—Ag—Re | 6 |
| Example 3-5 | Rh—Au—W | 8 |
| Example 3-6 | Pt—Au—Re | 7 |
| Example 3-7 | Ru—Ag—W | 11 |
| Example 3-8 | Ru—Au—Mo | 10 |
| Comparative Example 3-1 | Pd | 29 |

The catalysts used in the Examples were found to be stable with no substantial change in the properties even upon expiration of 500 hours from the initiation of the reaction.

PREPARATION EXAMPLE 4-1

Active carbon made of coconut shell was immersed in deionized water to impregnate water into pores thereof. This active carbon was put in 0.5 wt % hydrochloric acid. An aqueous solution having ruthenium chloride, diamine silver sulfate and chloroplatinic acid dissolved in a weight ratio of the respective metal components of 90:8:2 and in a total amount of the metal components of 2.0% by weight relative to the weight of the active carbon, was then gradually dropwise added thereto to have ion components adsorbed on the active carbon. An aqueous formalin solution was added thereto for reduction. Then, the active carbon was treated with an aqueous potassium hydroxide solution and washed with water. It was then dried at 150° C. for 5 hours.

PREPARATION EXAMPLE 4-2

Active carbon made of coconut shell was immersed in pure water to impregnate water into pores thereof. This active carbon was put in 0.5 wt % hydrochloric acid. An aqueous solution having ruthenium chloride, chloroauric acid and nickel chloride dissolved in a weight ratio of the respective metal components of 80:18:2 and in a total amount of the metal components of 2.0% by weight relative to the weight of the active carbon, was then gradually dropwise added thereto to have ion components adsorbed on the active carbon. An aqueous formalin solution was added thereto for reduction. Then, the active carbon was treated with an aqueous potassium hydroxide solution and washed with water.

PREPARATION EXAMPLE 4-3

Active carbon made of coconut shell was immersed in pure water to impregnate water into pores thereof. This active carbon was put in 0.5 wt % hydrochloric acid. An aqueous solution having ruthenium chloride, chloroauric acid and rhodium chloride dissolved in a weight ratio of the respective metal components of 80:15:5 and in a total amount of the metal components of 2.0% by weight relative to the weight of the active carbon, was then gradually dropwise added thereto to have ion components adsorbed on the active carbon. Then, the active carbon was washed with pure water and then dried at 150° C. for 5 hours. It was then further dried in nitrogen at 500° C. for 4 hours and then reduced by introducing hydrogen and maintaining it at 250° C. for 5 hours.

PREPARATION EXAMPLE 4-4

Active carbon made of coconut shell was immersed in pure water to impregnate water into pores thereof. An aqueous solution having rhodium chloride, copper chloride and potassium tungstate dissolved in a weight ratio of the respective metal components of 90:9:1 and in a total amount of the metal components of 1.0% by weight relative to the weight of the active carbon, was gradually dropwise added thereto to have ion components adsorbed on the active carbon. Sodium hydroxide and ethanol having sodium borohydride added thereto, were added for reduction. Hydrochloric acid was added to decompose excessive sodium borohydride. Then, the active carbon was washed with pure water and dried at 150° C. for 5 hours.

PREPARATION EXAMPLE 4-5

Active carbon made of coconut shell was immersed in pure water to impregnate water into pores thereof. This active carbon was put in 1 wt % hydrochloric acid. An aqueous solution having rhodium chloride, diamine silver sulfate and potassium perrhenate dissolved in a weight ratio of the respective metal components of 90:8:2 and in a total amount of the metal components of 2.0% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 4 hours.

PREPARATION EXAMPLE 4-6

Active carbon made of coconut shell was immersed in pure water to impregnate water into pores thereof. An aqueous solution having rhodium chloride, chloroauric acid and chloroplatinic acid dissolved in a weight ratio of the respective metal components of 80:18.5:1.5 and in a total amount of the metal components of 2.0% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 500° C. for 4 hours and then reduced by introducing hydrogen and maintaining it at 250° C. for 5 hours.

PREPARATION EXAMPLE 4-7

Active carbon made of coconut shell was immersed in pure water to impregnate water into pores thereof. An aqueous solution having rhodium chloride, chloroauric acid and potassium tungstate dissolved in a weight ratio of the respective metal components of 80:19.5:0.5 and in a total amount of the metal components of 2.0% by weight relative to the weight of the active carbon, was gradually dropwise added thereto to have ion components adsorbed on the active carbon. Sodium hydroxide and ethanol having sodium borohydride added thereto, were added for reduction. Hydrochloric acid was added thereto to decompose excessive sodium borohydride. Then, the active carbon was washed with pure water and then dried at 150° C. for 5 hours.

PREPARATION EXAMPLE 4-8

Active carbon made of coconut shell was immersed in pure water to impregnate water into pores thereof. An aqueous solution having palladium chloride, copper chloride and lanthanum chloride dissolved in a weight ratio of the respective metal components of 90:9:1 and in a total amount of the metal components of 1.0% by weight relative to the weight of the active carbon, was gradually dropwise added thereto to have ion components adsorbed on the active carbon. An aqueous formalin solution was added thereto, and the mixture was cooled under stirring and treated with potassium hydroxide. Then, the active carbon was washed with pure water and then dried at 150° C. for 5 hours.

PREPARATION EXAMPLE 4-9

Active carbon made of coconut shell was immersed in pure water to impregnate water into pores thereof. This active carbon was put in 1 wt % hydrochloric acid. An aqueous solution having palladium chloride, diamine silver sulfate and potassium perrhenate dissolved in a weight ratio of the respective metal components of 90:9.5:0.5 and in a total amount of the metal components of 0.5% by weight relative to the weight of the active carbon, was then gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 4-10

Active carbon made of coconut shell was immersed in pure water to impregnate water into pores thereof. An aqueous solution having palladium chloride, chloroauric acid and chloroplatinic acid dissolved in a weight ratio of the respective metal components of 90:9.9:0.1 and in a total amount of the metal components of 2.0% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 250° C. for 5 hours.

PREPARATION EXAMPLE 4-11

Active carbon made of coconut shell was immersed in pure water to impregnate water into pores thereof. An aqueous solution having palladium chloride, chloroauric acid and nickel chloride dissolved in a weight ratio of the respective metal components of 80:19:1 and in a total amount of the metal components of 2.0% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 4-12

Active carbon made of coconut shell was immersed in pure water to impregnate water into pores thereof. This active carbon was put in 1 wt % hydrochloric acid. An aqueous solution having chloroplatinic acid, copper chloride and potassium perrhenate dissolved in a weight ratio of the respective metal components of 80:19:1 and in a total amount of the metal components of 0.5% by weight relative to the weight of the active carbon, was gradually dropwise added thereto to have ion components adsorbed on the active carbon. An aqueous formalin solution was added thereto, and the mixture was cooled under stirring and then treated with an aqueous potassium hydroxide solution. Then, the active carbon was washed with pure water and then dried at 150° C. for 5 hours.

PREPARATION EXAMPLE 4-13

Active carbon made of coconut shell was immersed in pure water to impregnate water into pores thereof. An aqueous solution having chloroplatinic acid, diamine silver sulfate and potassium perrhenate dissolved in a weight ratio of the respective metal components of 80:18:2 and in a total amount of the metal components of 2.0% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

PREPARATION EXAMPLE 4-14

Active carbon made of coconut shell was immersed in pure water to impregnate water into pores thereof. An aqueous solution having chloroplatinic acid, chloroauric acid and potassium molybdenate dissolved in a weight ratio of the respective metal components of 90:9.8:0.2 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

COMPARATIVE PREPARATION EXAMPLE 4-1

Active carbon made of coconut shell was immersed in pure water to impregnate water into pores thereof. An aqueous solution having palladium chloride in a total amount of the metal components of 1.0% by weight relative to the weight of the active carbon, was gradually dropwise added thereto to have ion components adsorbed on the active carbon. An aqueous formalin solution was added thereto, and the mixture was cooled under stirring and treated with potassium hydroxide. Then, the active carbon was washed with pure water and then dried at 150° C. for 5 hours.

COMPARATIVE PREPARATION EXAMPLE 4-2

Active carbon made of coconut shell was immersed in pure water to impregnate water into pores thereof. An aqueous solution having palladium chloride dissolved in a total amount of the metal components of 2.0% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

COMPARATIVE PREPARATION EXAMPLE 4-3

Active carbon made of coconut shell was immersed in pure water to impregnate water into pores thereof. An aqueous solution having palladium chloride and nickel chloride (molar ratio: 1:1) dissolved in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

COMPARATIVE PREPARATION EXAMPLE 4-4

Active carbon made of coconut shell was immersed in pure water to impregnate water into pores thereof. An aqueous solution having ruthenium chloride dissolved in a total amount of the metal components of 0.5% by weight relative to the weight of the active carbon, was gradually dropwise added thereto to have ion components adsorbed on the active carbon. Then, active carbon was washed with pure water and then dried at 150° C. for 5 hours. It was then further dried in nitrogen at 550° C. for 4 hours and then reduced by introducing hydrogen and maintaining it at 300° C. for 5 hours.

EXAMPLES 4-1 TO 4-14

300 cc of the catalyst prepared in each Preparation Example was packed into a reaction tube made of Inconel 600 having an internal diameter of 2.54 cm and a length of 100 cm, and the reaction tube was immersed in a salt bath furnace.

Hydrogen and 2-chloro-1,1,1,2-tetrafluoroethane ($CF_3CHClF$) were introduced into the reaction tube in a molar ratio of 2:1. The flow rates of hydrogen and the starting material were 100 cc/min and 100 cc/min, respectively. The reaction temperature was 275° C., and the contact time was 20 seconds. The reaction product was collected in a trap cooled to −78° C. An acid content was removed from the collected product, and the composition was analyzed by gas chromatography and $^{19}F$-NMR. As a result, it was confirmed that the main reaction products were 1,1,1,2-tetrafluoroethane ($CF_3CH_2F$) and 1,1,1-trifluoroethane ($CF_3CH_3$). The reaction rate upon expiration of 200 hours from the initiation of the reaction is shown in Table 4-1.

COMPARATIVE EXAMPLES 4-1 TO 4-4

By using the catalyst prepared in each Comparative Preparation Example, the reaction was conducted and the composition of the gas at the outlet of the reaction tube was analyzed in the same manner as in the preceding Examples. As a result, it was confirmed that the main reaction products were 1,1,1,2-tetrafluoroethane ($CF_3CH_2F$) and 1,1,1-trifluoroethane ($CF_3CH_3$). The reaction rate upon expiration of 200 hours from the initiation of the reaction is shown in Table 4-2.

TABLE 4-1

|  | Catalyst composition | Reaction rate | Selectivity for R-134a (%) |
| --- | --- | --- | --- |
| Example 4-1 | Ru—Ag—Pt | 88 | 96 |
| Example 4-2 | Ru—Au—Ni | 87 | 96 |
| Example 4-3 | Ru—Au—Rh | 89 | 97 |
| Example 4-4 | Rh—Cu—W | 97 | 97 |
| Example 4-5 | Rh—Ag—Re | 96 | 97 |
| Example 4-6 | Rh—Au—Pt | 95 | 97 |
| Example 4-7 | Rh—Au—Mo | 94 | 97 |
| Example 4-8 | Pd—Cu—La | 96 | 97 |
| Example 4-9 | Pd—Ag—W | 97 | 97 |
| Example 4-10 | Pd—Au—Pt | 98 | 96 |
| Example 4-11 | Pd—Au—Ni | 97 | 96 |
| Example 4-12 | Pt—Cu—Re | 95 | 96 |
| Example 4-13 | Pt—Ag—Re | 97 | 96 |
| Example 4-14 | Pt—Au—Mo | 94 | 97 |

TABLE 4-2

|  | Catalyst composition | Reaction rate | Selectivity for R-134a (%) |
| --- | --- | --- | --- |
| Comparative Example 4-1 | Pd | 20 | 87 |
| Comparative Example 4-2 | Pd | 24 | 86 |
| Comparative Example 4-3 | Pd—Ni | 58 | 87 |
| Comparative Example 4-4 | Ru | 62 | 86 |

PREPARATION EXAMPLE 5-1

Active carbon made of coconut shell was immersed in pure water to impregnate water into pores thereof. An aqueous solution having palladium chloride and lanthanum chloride dissolved in a weight ratio of the respective metal components of 99:1 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 350° C. for 5 hours.

PREPARATION EXAMPLE 5-2

Active carbon made of coconut shell was immersed in pure water to impregnate water into pores thereof. An aqueous solution having palladium chloride and cerium chloride dissolved in a weight ratio of the respective metal components of 99:1 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 350° C. for 5 hours.

PREPARATION EXAMPLE 5-3

Active carbon made of coconut shell was immersed in pure water to impregnate water into pores thereof. An aqueous solution having chloroauric acid and lanthanum chloride dissolved in a weight ratio of the respective metal components of 98:2 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 700° C. for 5 hours.

PREPARATION EXAMPLE 5-4

Active carbon made of coconut shell was immersed in pure water to impregnate water into pores thereof. An aqueous solution having palladium chloride and neodium chloride dissolved in a weight ratio of the respective metal components of 99:1 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 600° C. for 5 hours.

PREPARATION EXAMPLE 5-5

Active carbon made of coconut shell was immersed in pure water to impregnate water into pores thereof. An aqueous solution having palladium chloride, potassium perrhenate and lanthanum chloride dissolved in a weight ratio of the respective metal components of 98:1:1 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 350° C. for 5 hours.

PREPARATION EXAMPLE 5-6

Active carbon made of coconut shell was immersed in pure water to impregnate water into pores thereof. An aqueous solution having palladium chloride and nickel chloride and lanthanum chloride dissolved in a weight ratio of the respective metal components of 90:9:1 and in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 350° C. for 5 hours.

COMPARATIVE PREPARATION EXAMPLE 5-1

Active carbon made of coconut shell was immersed in pure water to impregnate water into pores thereof. An aqueous solution having palladium chloride dissolved in a total amount of the metal components of 0.5% by weight relative to the weight of the active carbon, was gradually dropwise added thereto to have ion components adsorbed on the active carbon. Then, the active carbon was washed with pure water and then dried at 150° C. for 5 hours. It was then further dried in nitrogen at 550° C. for 4 hours and then reduced by introducing hydrogen and maintaining it at 300° C. for 5 hours.

EXAMPLES 5-1 TO 5-6

300 cc of the catalyst prepared in each Preparation Example was packed into a reaction tube made of Inconel 600 having an internal diameter of 2.54 cm and a length of 100 cm, and the reaction tube was immersed in a salt bath furnace.

Hydrogen and a starting material (2,2-dichloro-1,1,1,2-tetrafluoroethane and 1,2-dichloro-1,1,2,2-tetrafluoroethane) (molar ratio: 95:5) were introduced into the reaction tube in a molar ratio of 2:1. The flow rates of hydrogen and the starting material were 100 cc/min and 50 cc/min, respectively. The reaction temperature was 200° C., and the contact time was 10 seconds. The composition of the gas at the outlet of the reaction tube was analyzed by gas chromatography. As a result, it was confirmed that the main reaction products were R-124, R-134a and R-143a. The selectivity for R-143a among them is shown in Table 5-1.

COMPARATIVE EXAMPLE 5-1

By using the catalyst prepared in Comparative Preparation Example 5-1, the reaction was conducted and the composition of the gas at the outlet of the reaction tube was analyzed in the same manner as in the preceding Examples. As a result, it was confirmed that the main reaction products were R-124, R-134a and R-143a. The selectivity for R-143a among them is shown in Table 5-1.

TABLE 5-1

| | Catalyst composition | Selectivity for R-143a (%) |
|---|---|---|
| Example 5-1 | Pd—La | 9 |
| Example 5-2 | Pd—Ce | 8 |
| Example 5-3 | Pt—La | 9 |
| Example 5-4 | Pd—Nd | 8 |
| Example 5-5 | Pd—Re—La | 9 |
| Example 5-6 | Pd—Ni—La | 11 |
| Comparative Example 5-1 | Pd | 29 |

PREPARATION EXAMPLE 6-1

Active carbon made of coconut shell was immersed in pure water to impregnate water into pores thereof. This active carbon was put in 0.5 wt % hydrochloric acid. An aqueous solution having ruthenium chloride dissolved in a total amount of the metal components of 2.0% by weight relative to the weight of the active carbon, was then gradually dropwise added thereto to have ion components adsorbed on the active carbon. An aqueous formalin solution was added thereto for reduction. Then, the active carbon was treated with an aqueous potassium hydroxide solution and washed with water. It was then dried at 150° C. for 5 hours.

PREPARATION EXAMPLE 6-2

Molded active carbon made of coconut shell was immersed in a 0.5 wt % hydrochloric acid aqueous solution to impregnate water into pores thereof. Then, a catalyst was prepared in the same manner as in Preparation Example 6-1 except that an aqueous solution having ruthenium chloride and diamine silver sulfate dissolved in a weight ratio of the respective metal components of 90:10 and in a total amount of the metal components of 5% by weight relative to the weight of the active carbon, was used.

PREPARATION EXAMPLE 6-3

Molded active carbon made of coconut shell was immersed in a 0.5 wt % hydrochloric acid aqueous solution to impregnate water into pores thereof. Then, a catalyst was prepared in the same manner as in Preparation Example 6-1 except that an aqueous solution having ruthenium chloride and chloroauric acid dissolved in a weight ratio of the respective metal components of 90:10 and in a total amount of the metal components of 5% by weight relative to the weight of the active carbon, was used.

PREPARATION EXAMPLE 6-4

Active carbon made of coconut shell was immersed in pure water to impregnate water into pores thereof. An aqueous solution having rhodium chloride dissolved in a total amount of the metal components of 1.0% by weight relative to the weight of the active carbon, was gradually dropwise added thereto to have ion components adsorbed on the active carbon. Sodium hydroxide and ethanol having sodium borohydride added thereto, were added for reduction. Hydrochloric acid was added to decompose excessive sodium borohydride. Then, the active carbon was washed with pure water and dried at 150° C. for 5 hours.

PREPARATION EXAMPLE 6-5

Molded active carbon made of coconut shell was immersed in a 0.5 wt % hydrochloric acid aqueous solution to impregnate water into pores thereof. Then, a catalyst was prepared in the same manner as in Preparation Example 6-4 except that an aqueous solution having rhodium chloride and diamine silver sulfate dissolved in a weight ratio of the respective metal components of 90:10 and in a total amount of the metal components of 1% by weight relative to the active carbon, was used.

PREPARATION EXAMPLE 6-6

Pulverized active carbon made of coconut shell was immersed in a 1 wt % hydrochloric acid aqueous solution to impregnate water into pores thereof. Then, a catalyst was prepared in the same manner as in Preparation Example 6-4 except that an aqueous solution having rhodium sulfate and chloroauric acid dissolved in a weight ratio of the respective metal components of 90:10 and in a total amount of the metal components of 1% by weight relative to the weight of the active carbon, was used.

PREPARATION EXAMPLE 6-7

Pulverized active carbon made of coconut shell was immersed in a 0.5 wt % hydrochloric acid aqueous solution to impregnate water into pores thereof. An aqueous solution having palladium chloride dissolved in a total amount of the metal components of 2.0% by weight relative to the weight of the active carbon, was gradually dropwise added thereto to have ion components adsorbed on the active carbon. An aqueous solution containing 30% by weight of hydrazine was dropwise added thereto for rapid reduction. Then, the active carbon was washed with pure water and dried at 150° C. for 5 hours.

PREPARATION EXAMPLE 6-8

Pulverized active carbon made of coconut shell was immersed in a 0.5 wt % hydrochloric acid aqueous solution to impregnate water into pores thereof. An aqueous solution having palladium chloride and chloroauric acid dissolved in a weight ratio of the respective metal components of 99.9:0.1 and in a total amount of the metal components of 0.1% by weight relative to the weight of the active carbon, was gradually dropwise added thereto to have ion components adsorbed on the active carbon. An aqueous solution containing 30% by weight of hydrazine was dropwise added for rapid reduction. Then, the active carbon was washed with pure water and dried at 150° C. for 5 hours.

PREPARATION EXAMPLE 6-9

Molded active carbon made of coconut shell was immersed in a 1 wt % hydrochloric acid aqueous solution to impregnate water into pores thereof. Then, a catalyst was prepared in the same manner as in Preparation Example 6-7 except that an aqueous solution having palladium chloride and rhodium chloride dissolved in a weight ratio of the respective metal components of 99:1 and in a total amount of the metal components of 0.5% by weight relative to the weight of the active carbon, was used.

PREPARATION EXAMPLE 6-10

Pulverized active carbon made of coconut shell was immersed in a 0.5 wt % hydrochloric acid aqueous solution to impregnate water into pores thereof. Then, a catalyst was prepared in the same manner as in Preparation Example 6-7 except that an aqueous solution having palladium chloride and copper sulfate dissolved in a weight ratio of the respective metal components of 90:10 and in a total amount of the metal components of 1% by weight relative to the weight of the active carbon, was used.

PREPARATION EXAMPLE 6-11

Active carbon made of coconut shell was immersed in pure water to impregnate water into pores thereof. This active carbon was put in a 1 wt % hydrochloric acid aqueous solution. Then, an aqueous solution having chloroauric acid dissolved in a total amount of the metal components of 0.5 % by weight relative to the active carbon, was gradually dropwise added thereto to have ion components adsorbed on the active carbon. An aqueous formalin solution was added thereto, and the mixture was cooled under stirring and then treated with an aqueous potassium hydroxide solution. The active carbon was washed with pure water and then dried at 150° C. for 5 hours.

PREPARATION EXAMPLE 6-12

Molded active carbon made of coconut shell was immersed in a 1.0 wt % hydrochloric acid aqueous solution to impregnate water into pores thereof. Then, a catalyst was prepared in the same manner as in Preparation Example 6-11 except that an aqueous solution having chloroplatinic acid and diamine silver sulfate dissolved in a weight ratio of the respective metal components of 90:10 and in a total amount of the metal components of 2% by weight relative to the weight of the active carbon, was used.

PREPARATION EXAMPLE 6-13

Molded active carbon made of coconut shell was immersed in a 1 wt % hydrochloric acid aqueous solution to impregnate water into pores thereof. Then, a catalyst was prepared in the same manner as in Preparation Example 6-11 except that an aqueous solution having chloroplatinic acid and chloroauric acid dissolved in a weight ratio of the respective metal components of 90:10 and in a total amount of the metal components of 1% by weight relative to the weight of the active carbon, was used.

COMPARATIVE PREPARATION EXAMPLE 6-1

Molded active carbon made of coconut shell (Shirasagi $C_2X$) was immersed in a 0.5 wt % hydrochloric acid aqueous solution to impregnate water into pores thereof. An aqueous solution having ruthenium chloride dissolved in a total amount of the metal components of 2.0% by weight relative to the weight of the active caron, was gradually dropwise added thereto to have ion components adsorbed on the active carbon. Then, the active carbon was washed with pure water and dried at 150° C. for 5 hours. It was then further dried in nitrogen at 250° C. for 4 hours and then reduced by introducing hydrogen and maintaining it at 350° C. for 4 hours.

COMPARATIVE PREPARATION EXAMPLE 6-2

Molded active carbon made of coconut shell (Shirasagi C₂X) was immersed in a 0.5 wt % hydrochloric acid aqueous solution to impregnate water into pores thereof. An aqueous solution having rhodium chloride dissolved in a total amount of the metal components of 0.1% by weight relative to the weight of the active caron, was gradually dropwise added thereto to have ion components adsorbed on the active carbon. Then, the active carbon was washed with pure water and dried at 150° C. for 5 hours. It was then further dried in nitrogen at 250° C. for 4 hours and then reduced by introducing hydrogen and maintaining it at 350° C. for 5 hours.

COMPARATIVE PREPARATION EXAMPLE 6-3

Molded active carbon made of coconut shell (Shirasagi C₂X) was immersed in a pure water to impregnate water into pores thereof. An aqueous solution having palladium chloride dissolved in a total amount of the metal components of 2.0% by weight relative to the weight of the active caron, was gradually dropwise added thereto to have ion components adsorbed on the active carbon. Then, the active carbon was washed with pure water and dried at 150° C. for 5 hours. It was then further dried in nitrogen at 250° C. for 4 hours and then reduced by introducing hydrogen and maintaining it at 350° C. for 5 hours.

COMPARATIVE PREPARATION EXAMPLE 6-4

Molded active hydrocarbon made of coconut shell (Shirasagi C₂X) was immersed in a 0.5 wt % hydrochloric acid aqueous solution to impregnate water into pores thereof. An aqueous solution having chloroplatinic acid dissolved in a total amount of the metal components of 0.5% by weight relative to the weight of the active caron, was gradually dropwise added thereto to have ion components adsorbed on the active carbon. Then, the active carbon was washed with pure water and dried at 150° C. for 5 hours. It was then further dried in nitrogen at 250° C. for 4 hours and then reduced by introducing hydrogen and maintaining it at 350° C. for 5 hours.

EXAMPLES 6-1 TO 6-13

300 cc of the catalyst prepared in each Preparation Example was packed into a reaction tube made of Inconel 600 having an internal diameter of 2.54 and a length of 100 cm, and the reaction tube was immersed in a salt bath furnace.

Hydrogen and a starting material (comprising 2,2-dichloro-1,1,1,2-tetrafluoroethane and 1,2-dichloro-1,1,2,2-tetrafluoroethane in a molar ratio of 95:5) were introduced into the reaction tube in a molar ratio of 2:1. The flow rates of hydrogen and the starting material were 100 cc/min and 50 cc/min, respectively. The reaction temperature was 220° C., and the contact time was 20 seconds. The composition of the gas at the outlet of the reaction tube was analyzed by gas chromatography. As a result, it was confirmed that the main reaction products were R-124, HCFC-134a and R-143a. The selectivity for R-114a among them is shown in Table 6-1.

COMPARATIVE EXAMPLES 6-1 TO 6-4

By using the catalyst prepared in each Comparative Preparation Example, the reaction was conducted and the composition of the gas at the outlet of the reaction tube was analyzed in the same manner as in the preceding Examples. As a result, it was confirmed that the main reaction products were R-124, R-134a and R-143a. The selectivity for R-143a among them is shown in Table 6-2.

TABLE 6-1

|  | Reaction rate for R-114a (%) |
|---|---|
| Example 6-1 | 52 |
| Example 6-2 | 51 |
| Example 6-3 | 53 |
| Example 6-4 | 89 |
| Example 6-5 | 89 |
| Example 6-6 | 86 |
| Example 6-7 | 86 |
| Example 6-8 | 88 |
| Example 6-9 | 87 |
| Example 6-10 | 86 |
| Example 6-11 | 95 |
| Example 6-12 | 92 |
| Example 6-13 | 91 |

TABLE 6-2

|  | Reaction rate for R-114a (%) |
|---|---|
| Comparative Example 6-1 | 21 |
| Comparative Example 6-2 | 52 |
| Comparative Example 6-3 | 58 |
| Comparative Example 6-4 | 49 |

What is claimed is:

1. A process for producing 1,1,1,2-tetrafluoroethane, which comprises:

reacting 2,2-dichloro-1,1,1,2-tetrafluoroethane, 2-chloro-1,1,1,2-tetrafluoroethane or a mixture thereof with hydrogen in the presence of a hydrogenation catalyst consisting essentially of a Group VIII element selected from the group consisting of Pt, Pd, Ni, Rh, Co, Ru and Ir as the main component and at least one element selected from the group consisting of Cu, Ag, Au, La, Ce and Nd in an amount ranging from 0.1 to 30% by weight as an additional component.

2. The process according to claim 1, wherein the hydrogenation catalyst supported on a carrier selected from the group consisting of active carbon carrier, alumina carrier and zirconia carrier.

3. The process according to claim 1, wherein the reaction is conducted in the gas phase at a temperature of from 120° to 450° C.

4. The process according to claim 1, wherein the hydrogenation catalyst is prepared by a wet reduction method.

5. A process for producing 1,1,1,2-tetrafluoroethane, which comprises:

reacting 2,2-dichloro-1,1,1,2-tetrafluoroethane, 2-chloro-1,1,1,2-tetrafluoroethane or a mixture thereof with hydrogen in the presence of a hydrogenation catalyst consisting essentially of a Group VIII element selected from the group consisting of Pt, Pd, Ni, Rh, Co, Ru and Ir as the main component and at least one element selected from the group consisting of Cu, Ag, Au, La, Ce and Nd in an amount ranging from 0.1 to 30% by weight as a first additional component and at least one high melting point metal element selected from the group consisting Group VIII elements other than the element employed as the main component, Ni, Co, Re, W, Ta, Nb, Ti, Zr and Mo as a second additional catalyst component in an amount ranging from 0.1 to 10% by weight.

6. The process according to claim 5, wherein the hydrogenation catalyst is supported on a carrier selected from the group consisting of active carbon carrier, alumina carrier and zirconia carrier.

7. The process according to claim 5, wherein the reaction is conducted in the gas phase at a temperature of from 120° to 450° C.

8. The process of claim 5, wherein the hydrogenation catalyst is prepared by a wet reduction method.

9. A process for producing 1,1,1,2-tetrafluoroethane, which comprises:

reacting 2,2-dichloro-1,1,1,2-tetrafluoroethane, 2-chloro-1,1,1,2-tetrafluoroethane or a mixture thereof with hydrogen in the presence of a hydrogenation catalyst consisting essentially of a Group VIII element selected from the group consisting of Pt, Pd, Ni, Rh, Co, Ru and Ir as the main component and at least one element selected from the group consisting of Cu, Ag, Au, La, Ce and Nd in an amount ranging from 0.1 to 30% by weight as an additional component supported on a carrier.

* * * * *